United States Patent [19]

Chaturvedula

[11] Patent Number: 5,663,312
[45] Date of Patent: Sep. 2, 1997

[54] OLIGONUCLEOTIDE DIMERS WITH AMIDE LINKAGES REPLACING PHOSPHODIESTER LINKAGES

[75] Inventor: Prasad Venkata Chala Chaturvedula, Exton, Pa.

[73] Assignee: Sanofi, France

[21] Appl. No.: 361,241

[22] Filed: Dec. 20, 1994

Related U.S. Application Data

[63] Continuation of Ser. No. 40,826, Mar. 31, 1993, abandoned.

[51] Int. Cl.$^6$ .......................... C07H 19/00; C07H 21/00; C07H 21/02; C07H 21/04
[52] U.S. Cl. .......................... 536/22.1; 536/24.3; 536/25.6
[58] Field of Search .................................. 435/6; 514/44; 536/22.1, 23.1, 24.1, 24.3, 24.5, 25.6

[56] References Cited

FOREIGN PATENT DOCUMENTS

92/20823  11/1992  WIPO.

OTHER PUBLICATIONS

Gura "Antisense has growing pains" Science 270:575–577 Oct. 27, 1995.
Milligan et al. "Current concepts in Antisense drug design" J. Medicinal Chem. 36(14):1923–1927 Jul. 9, 1993.

*Primary Examiner*—John L. LeGuyader
*Assistant Examiner*—Thomas G. Larson
*Attorney, Agent, or Firm*—Paul E. Dupont; William J. Davis

[57] ABSTRACT

Disclosed are oligonucleotide analogs comprising oligonucleoside sequences having from 3 to about 200 bases and containing internucleoside linkages wherein amide linkages replace phosphodiester linkages that are the backbones of the natural oligonucleotides that make up RNA and DNA. Also disclosed are bifunctional nucleoside analogs, a process for preparing dimers and trimers therefrom, and a method of using these bifunctional nucleoside intermediates, including the dimers and trimers, to synthesize the above-described oligonucleotide analogs using conventional synthetic organic procedures known in the art, preferably in a solid phase synthesis, more preferably in an automated peptide synthesizer.

2 Claims, No Drawings

OLIGONUCLEOTIDE DIMERS WITH AMIDE LINKAGES REPLACING PHOSPHODIESTER LINKAGES

This application is a continuation of application Ser. No. 08/040,826, filed Mar. 31, 1993, now abandoned.

FIELD OF THE INVENTION

The present invention relates to oligonucleotide analogs comprising oligonucleoside sequences having from 3 to about 60 bases and containing internucleoside linkages wherein amide linkages replace phosphodiester linkages that are the backbones of the natural oligonucleotides that make up RNA and DNA. The present invention also relates to bifunctional nucleoside analogs, a process for preparing dimers and trimers therefrom, and to a method of using these bifunctional nucleoside intermediates, including the dimers and trimers, to synthesize the above-described oligonucleotide analogs using conventional synthetic organic procedures known in the art, preferably in a solid phase synthesis, more preferably in an automated peptide synthesizer.

BACKGROUND OF THE INVENTION

An antisense compound binds to or hybridizes with a nucleotide sequence in a nucleic acid (RNA or DNA) to inhibit the function (or synthesis) of the nucleic acid. Because they can hybridize with both RNA and DNA, antisense compounds can interfere with gene expression at the level of transcription, RNA processing or translation.

As discussed, e.g., in Klausner, A., Biotechnology, 8:303–304 (1990), the development of practical applications of antisense technology is hampered by a number of technical problems. Thus, natural, phosphodiester-linked antisense oligomer compounds are susceptible to rapid degradation by nucleases that exist in target cells and elsewhere in the body; both exonucleases, which act on either the 3' or the 5' terminus of the nucleic acid, and endonucleases, which cleave the nucleic acid at internal phosphodiester linkages between individual nucleosides. As a result of such nuclease action, the effective half life of many administered antisense compounds is very short, necessitating the use of large, frequently administered, doses.

The high cost of producing antisense DNA or RNA on currently available DNA synthesizers is another problem. Armstrong, L., Business Week, Mar. 5, 1990, page 89, estimated the cost of producing one gram of antisense DNA to be about $100,000.

There is also a problem regarding delivery of antisense agents to targets within the body (and cell). Thus, antisense agents targeted to genomic DNA must permeate the plasma and the nuclear membrane to gain access to the nucleus. The consequent need for increased hydrophobicity to enhance membrane permeability must be balanced against the need for increased hydrophilicity (water solubility) in body fluids such as the plasma and cell cytosol.

Also, oligonucleotide compounds such as antisense DNA are susceptible to steric reconfiguration around chiral phosphorous centers. This results in stability problems, too, whether the compounds are free within the body or hybridized to target nucleic acids.

To overcome the stability and drug delivery limitations, various oligonucleotide analogs have been investigated. In order to be of practical utility, such analogs should have good cell penetration properties, be resistant to nuclease degradation, have good sequence specific hybridization to target nucleic acids, and be synthesizable by chemical methods that are not too difficult or costly.

Recent efforts to overcome the foregoing problems and prepare antisense compounds that are stable, nuclease resistant, relatively inexpensive to manufacture and which can be delivered to and hybridized with nucleic acid targets throughout the body have involved synthesizing oligonucleotide analogs that consist of oligonucleoside sequences with internucleoside linkages that differ from the 'normal' internucleoside phosphodiester linkage, either by introducing modifications in the phosphodiester structure or by using non-phosphate internucleoside linkages that approximate the length and orientation of the normal phosphodiester internucleoside linkage. Uhlman, E. and Peyman, A., Chemical Reviews, 9(4):544–584 (1990).

Among the modified phosphodiester linkages that have been reported are phosphorothioates, alkylphosphotriesters, methylphosphonates and alkylphosphoramidates. Also, a variety of non-ionic oligonucleosides sequences containing non-phosphate internucleoside linkages, such as carbonate, acetate, carbamate, sulfone, sulfoxide, sulfonamide and dialkyl- or diaryl- silyl derivatives have been synthesized and reported. More recently, chimeric oligonucleotide analogs comprising nucleoside linkages containing two carbon atoms and one nitrogen atom or one oxygen atom, as well as those containing three carbon atoms, have been reported. See, e.g., International Patent Publication WO 9202534.

The present invention provides oligonucleosides of three bases and longer uniformly substituted with internucleoside linkages wherein amide linkages replace phosphodiester linkages that are the backbones of the natural oligonucleotides that make up RNA and DNA. The present invention also provides chimeric oligonucleotide analogs comprising oligonucleoside sequences having from 3 to about 200 bases and containing internucleoside linkages wherein amide linkages replace phosphodiester linkages that are the backbones of the natural oligonucleotides that make up RNA and DNA. The present invention also relates to bifunctional nucleoside analogs, a process for preparing dimers and trimers therefrom, and to a method of using these bifunctional nucleoside intermediates, including the dimers and trimers, to synthesize the above-described oligonucleotide analogs using conventional synthetic organic procedures known in the art, preferably in a solid phase synthesis, more preferably in an automated peptide synthesizer.

As used herein, the term 'oligonucleotide' means nucleic acid compounds which contain only 'natural' phosphodiester internucleoside linkages. On the other hand, the term 'chimeric oligonucleotide analogs' means compounds that comprise sequences containing both oligonucleoside linkages and phosphodiester oligonucleotide linkages. By the term 'oligonucleosides,' we mean oligonucleotide analogs that contain only synthetic (as opposed to the naturally occurring phosphodiester) internucleoside linkages.

SUMMARY OF THE INVENTION

The present invention provides novel nucleoside intermediates, and dimers and trimers thereof that are useful for preparing oligonucleotide analogs comprising oligonucleoside sequences having from 3 to about 60 bases that contain iternucleoside linkages wherein amide linkages replace phosphodiester linkages that are the backbones of the natural oligonucleotides that make up RNA and DNA. The present invention also involves a process for preparing dimers and trimers having amide internucleoside linkages and of using them to synthesize the above-described oligonucleotide analogs using conventional synthetic organic procedures, preferably in a solid phase synthesis, more preferably in an automated peptide synthesizer. The preparation of bifunctional nucleoside intermediates in accordance with the invention is illustrated in Scheme 1; the synthesis of dimer and trimer oligonucleotide analog compounds in accordance with this invention, as well as that of longer oligonucleotide analogs therefrom, is illustrated in Scheme 2.

More particularly, the present invention provides novel oligonucleotide analogs of Formula I below:

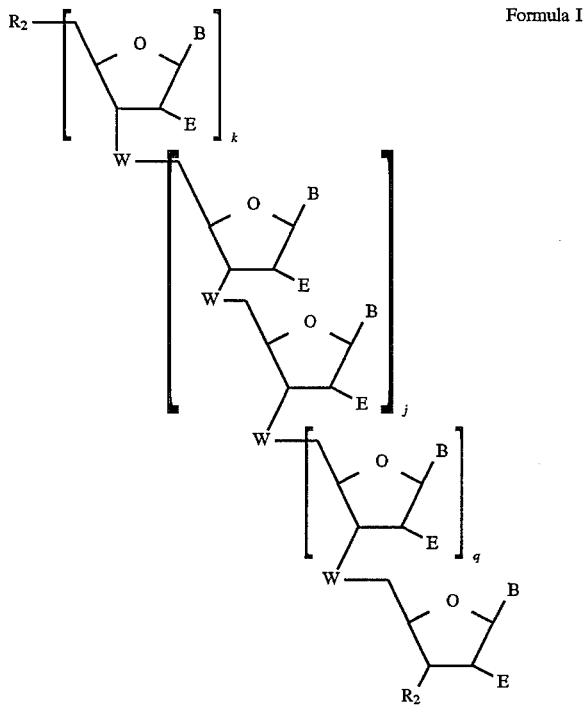

Formula I wherein
- each $R_2$ is selected from the group consisting of H, OH, $NR_3R_4$, CHO, hydroxy-lower alkyl, carbalkoxy-lower alkyl, carboxy- lower alkyl, lower alkenyl, amino-lower alkyl, lower alkyl, protected aldehyde and halogen;
- each E is selected from the group consisting of H, OZ, SZ, and NHZ;
- each Z is selected from the group consisting of H, lower alkyl, lower alkenyl, aryl, acyl, and O-, S-, and N-protecting groups;
- each B is independently select from the group consisting of adenine, cytosine, guanine, thymine, uracil or a modification thereof that does not substantially interfere with the affinity of an oligonucleoside or chimeric oligonucleotide analog for its antisense counterpart wherein the bases are selected from the group consisting of adenine, cytosine, guanine, thymine and uracil;
- each W is an internucleoside linkage selected from the group consisting of
  (1) -3'-$(CR_3R_4)_m$-$CONR_1$-$(CR_3R_4)_n$-5'-,
  (2) -3'-$(OR_3R_4)_m$-$NR_1CO$-$(CR_3R_4)_n$-5'-, and
  (3) a natural phosphodiester internucleoside linkage, with the proviso that at least one W is internucleoside linkage (1) or (2);
- each $R_1$, $R_3$, and $R_4$ is selected from the group consisting of H, lower alkyl, aryl, aryl-lower alkyl, and lower alkenyl;
- m and n are independently 0, 1 or 2, with the proviso that the sum of m+n is 2;
- j is an integer from 1 to 30;
- k is 0 or an integer from 1 to 60; and
- q is 0 or an integer from 1 to 60, with the proviso that the sum of j+k+q is from 3 to about 60.

The invention also provides bifunctional dimers having the structure of Formula II:

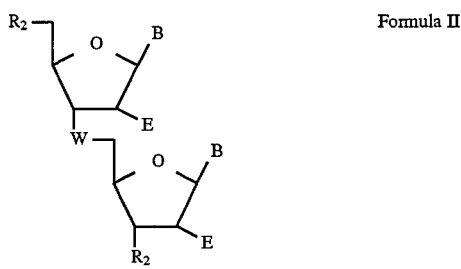

Formula II wherein:
- each $R_2$ is selected from the group consisting of H, OH, $NR_3R_4$, CHO, hydroxy-lower alkyl, carbalkoxy-lower alkyl, carboxy- lower alkyl, lower alkenyl, amino-lower alkyl, lower alkyl, protected aldehyde and halogen;
- each E is selected from the group consisting of H, OZ, SZ, and NHZ;
- each Z is selected from the group consisting of H, lower alkyl, lower alkenyl, aryl, acyl, and O-, S-, and N-protecting groups;
- each B is independently select from the group consisting of adenine, cytosine, guanine, thymine, uracil or a modification thereof that does not substantially interfere with the affinity of an oligonucleoside or chimeric oligonucleotide analog for its antisense counterpart wherein the bases are selected from the group consisting of adenine, cytosine, guanine, thymine and uracil;
- W is an internucleoside linkage selected from -3'-$(CR_3R_4)_m$-$CONR_1$-$(CR_3R_4)_n$-5'- and -3'-$(CR_3R_4)_m$-$NR_1CO$-$(CR_3R_4)_n$-5'-;
- each $R_1$, $R_3$, and $R_4$ is selected from the group consisting of H, lower alkyl, aryl, aryl-lower alkyl, and lower alkenyl; and
- m and n are independently 0, 1 or 2, with the proviso that the sum of m+n is 2.

DETAILED DESCRIPTION OF THE INVENTION

The bifunctional dimers of the invention have the structure of Formula II:

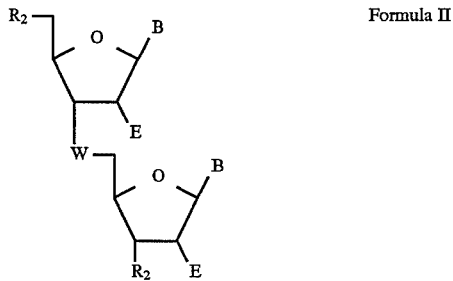

Formula II wherein:
- each $R_2$ is selected from the group consisting of H, OH, $NR_3R_4$, CHO, hydroxy-lower alkyl, carbalkoxy-lower alkyl, carboxy- lower alkyl, lower alkenyl, amino-lower alkyl, lower alkyl, protected aldehyde and halogen;

each E is selected from the group consisting of H, OZ, SZ, and NHZ;

each Z is selected from the group consisting of H, lower alkyl, lower alkenyl, aryl, acyl, and O-, S-, and N-protecting groups;

each B is independently select from the group consisting of adenine, cytosine, guanine, thymine, uracil or a modification thereof that does not substantially interfere with the affinity of an oligonucleoside or chimeric oligonucleotide analog for its antisense counterpart wherein the bases are selected from the group consisting of adenine, cytosine, guanine, thymine and uracil;

W is an internucleoside linkage selected from
-3'-$(CR_3R_4)_m$-$CONR_1$-$(CR_3R_4)_n$-5'- and
-3'-$(CR_3R_4)_m$-$NR_1CO$-$(CR_3R_4)_n$-5'-;

each $R_1$, $R_3$, and $R_4$ is selected from the group consisting of H, lower alkyl, aryl, aryl-lower alkyl, and lower alkenyl; and m and n are independently 0, 1 or 2, with the proviso that the sum of m+n is 2.

The oligonucleosides and oligonucleotide analogs of the present invention have the Formula I:

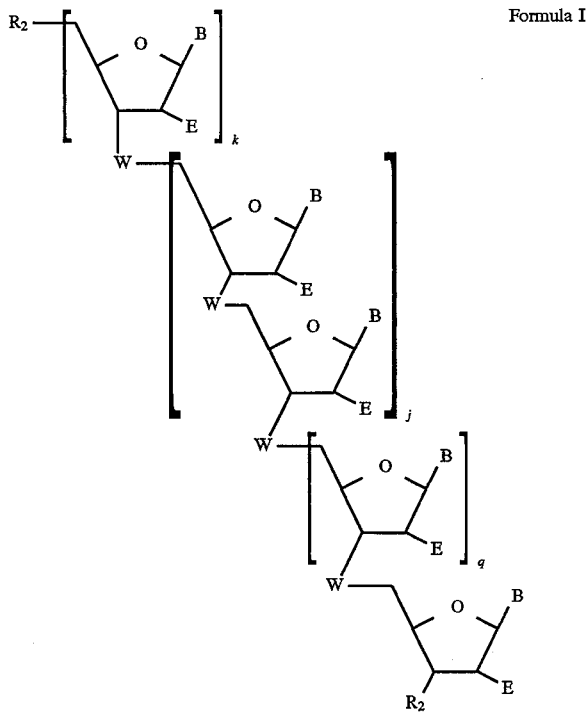

Formula I wherein each $R_2$ is selected from the group consisting of H, OH, $NR_3R_4$, CHO, hydroxy-lower alkyl, carbalkoxy-lower alkyl, carboxy- lower alkyl, lower alkenyl, amino-lower alkyl, lower alkyl, protected aldehyde and halogen;

each E is selected from the group consisting of H, OZ, SZ, and NHZ;

each Z is selected from the group consisting of H, lower alkyl, lower alkenyl, aryl, acyl, and O-, S-, and N-protecting group;

each B is independently select from the group consisting of adenine, cytosine, guanine, thymine, uracil or a modification thereof that does not substantially interfere with the affinity of an oligonucleoside or chimeric oligonucleotide analog for its antisense counterpart wherein the bases are selected from the group consisting of adenine, cytosine, guanine, thymine and uracil;

each W is an internucleoside linkage selected from the group consisting of
(1) -3'-$(CR_3R_4)_m$-$CONR_1$-$(OR_3R_4)_n$-5'-,
(2) -3'-$(CR_3R_4)_m$-$NR_1CO$-$(CR_3R_4)_n$-5'-, and
(3) a natural phosphodiester internucleoside linkage, with the proviso that at least one W is internucleoside linkage (1) or (2);

each $R_1$, $R_3$, and $R_4$ is selected from the group consisting of H, lower alkyl, aryl, aryl-lower alkyl, and lower alkenyl;

m and n are independently 0, 1 or 2, with the proviso that the sum of m+n is 2;

j is an integer from 1 to 30;

k is 0 or an integer from 1 to 60; and q is 0 or an integer from 1 to 60, with the proviso that the sum of j+k+q is from 3 to about 60.

As employed above and throughout the disclosure, the following terms, unless otherwise indicated, shall be understood to have the following meanings:

"Alkyl" means a saturated aliphatic hydrocarbon which may be either straight- or branched-chain. Preferred groups have no more than about 12 carbon atoms and may be methyl, ethyl and structural isomers of propyl, butyl, pentyl, hexyl, heptyl, octyl, nonyl, decyl, undecyl and dodecyl.

"Lower alkyl" means an alkyl group as above, having 1 to 7 carbon atoms. Suitable lower alkyl groups are methyl, ethyl, n-propyl, isopropyl, butyl, tert-butyl, n-pentyl, neopentyl, n-hexyl, and n-heptyl.

"Aryl" means phenyl, naphthyl, substituted phenyl and substituted naphthyl.

"Substituted phenyl (or naphthyl)" means a phenyl (or naphthyl) group in which one or more of the hydrogens has been replaced by the the same or different substituents selected from halo, lower alkyl, nitro, amino, acylamino, hydroxyl, lower alkoxy, aryl, heteroaryl, lower alkoxy, alkylsulfonyl, and trifluoromethyl.

"Heteroaryl group" means, pyridyl, furyl, thienyl, or imidazolyl.

"Substituted heteroaryl" means a heteroaryl group in which one or more of the hydrogens has been replaced by the the same or different substituents selected from halo, lower alkyl, nitro, amino, acylamino, hydroxyl, lower alkoxy, aryl, heteroaryl, lower alkoxy, alkylsulfonyl, and trifluoromethyl.

"Lower alkenyl" means an unsaturated aliphatic hydrocarbon having 2 to 8 carbon atoms, such as ethylene, propylene, butylene, isobutylene, etc., including all structural and geometrical isomers thereof.

"Halo" means bromo, chloro or fluoro.

An "O-, S-, or N-protecting group" is a radical attached to an oxygen, sulfur, or nitrogen atom, respectively, which radical serves to protect the oxygen, sulfur, or nitrogen functionality against undesired reaction. Such protecting groups are well known in the art; many are described in "The Peptides." E. Gross and J. Meienhofer, Eds. Vol 3 Academic Press, NY (1981). The N-protecting groups can be N-acyl, N-alkoxycarbonyl, N-arylmethoxy-carbonyl, trifluoromethylacyl and N-arylsulfonyl protecting groups. Suitable O-protecting groups include benzyl, tert-butyl, methyl, tosyl, dimethoxytrityl, tert-butyl-dimethylsilyl, and carbobenzoxy groups. S-Protecting groups include methyl, tert-butyl, benzyl, and carbobenzoxy groups.

Pharmaceutically acceptable salts include both acid and base addition salts. "Pharmaceutically acceptable salt" refers to those salts which retain the biological effectiveness and properties of the free bases and which are not biologically or otherwise undesirable. Suitable pharmaceutically acceptable acid addition salts can be formed with inorganic acids such as hydrochloric acid, hydrobromic acid, sulfuric acid, nitric acid, phosphoric acid, and the like, and organic acids such as acetic acid, propionic acid, glycolic acid, pyrubic acid, fumaric acid, tartaric acid, citric acid, bonzoic acid, cinnamic acid, mandelic acid, methanosulfonic acid, and p-toluonesulfonic acid, and the like.

Pharmaceutically acceptable base addition salts include those derived from inorganic bases such as sodium, potassium, lithium, ammonium, calcium, magnesium, iron, zinc, copper, manganese, aluminum salts and the like. Particularly preferred am the ammonium, potassium, sodium, calcium and magnesium salts. Salts derived from pharmaceutically acceptable organic non-toxic bases include salts of primary, secondary, and tertiary amines, substituted amines, including naturally occuring substituted amines, cyclic amines and basic ion exchange resins, such as isopropylamino, tripropylamine, ethanolamine, 2-diethylaminoethanol, 2-dimethylaminoethanol, dicyclohexylamino, lysine, arginine, histidine, caffeine, procain, hydrabamine, choline, betaine, ethylenediamine, glucosamine, methylglucamine, theobromine, purines, peperizines, piperidine, polyamine resins and the like. Particularly preferred organic non-toxic bases are isopropylamine, diethylamine, ethanol-amine and dicyclohexylamine.

This invention also contemplates pharmaceutically acceptable acid-addition salts of the compounds of Formula I. It is well known in the pharmacological arts that nontoxic addition salts of pharmacologically active amine compounds do not differ in activities from their free base.

The present invention also provides a process for preparing the above-described oligonucleoside and chimeric oligonucleotide analog compounds using the dimeric nucleoside compounds of this invention, this process comprising joining a 5'-end nucleoside, a middle, bifunctional, unit and a 3'-end nucleoside, by conventional synthetic organic methods known in the art, to produce various oligomers which are are useful as antisense compounds.

As shown in Scheme 1, four key bifunctional intermediate nucleosides, 2, 5, 7, and 10, which may be prepared by the procedure outlined, contain an amino group in either the 3'- or 5'- position and, correspondingly, a carboxy group in the 5' or 3' position. As depicted in Scheme 2, these amino functional groups will undergo coupling reactions with a carboxy group of another, similar nucleoside to afford novel dimer analogs possessing an amidoalkylene internucleotide linkage instead of the naturally occuring phosphodiester linkage. A further novel aspect of this invention are previously undescribed dimers 12 and 15 and trimers 13 and 16. These are also critical intermediates in the synthesis of the amide linked oligonucleosides and chimeric oligonucleotide analogs of the invention.

Referring to Scheme 2, coupling of 3'-amino-nucleoside 7 and the 6'-carboxyl-nucleoside 11 will afford a new amidodimer 12. Subsequent treatment of 3'-amino-nucleoside 7 with the dimer-acid 12 yields a novel amido-trimer 13 as shown. Another type of amido-linked trimer 16 is prepared by reaction of 3'-acid 14 with 5'-amino-nucleoside 10 to yield dimer intermediate 15 which, after hydrogenolysis, undergoes a coupling reaction with 3'-acid 14 to afford trimer 16. The illustrated synthetic reactions may be employed for the preparation of various tetramers and longer oligomers containing the amido-alkylene internucleoside linkage.

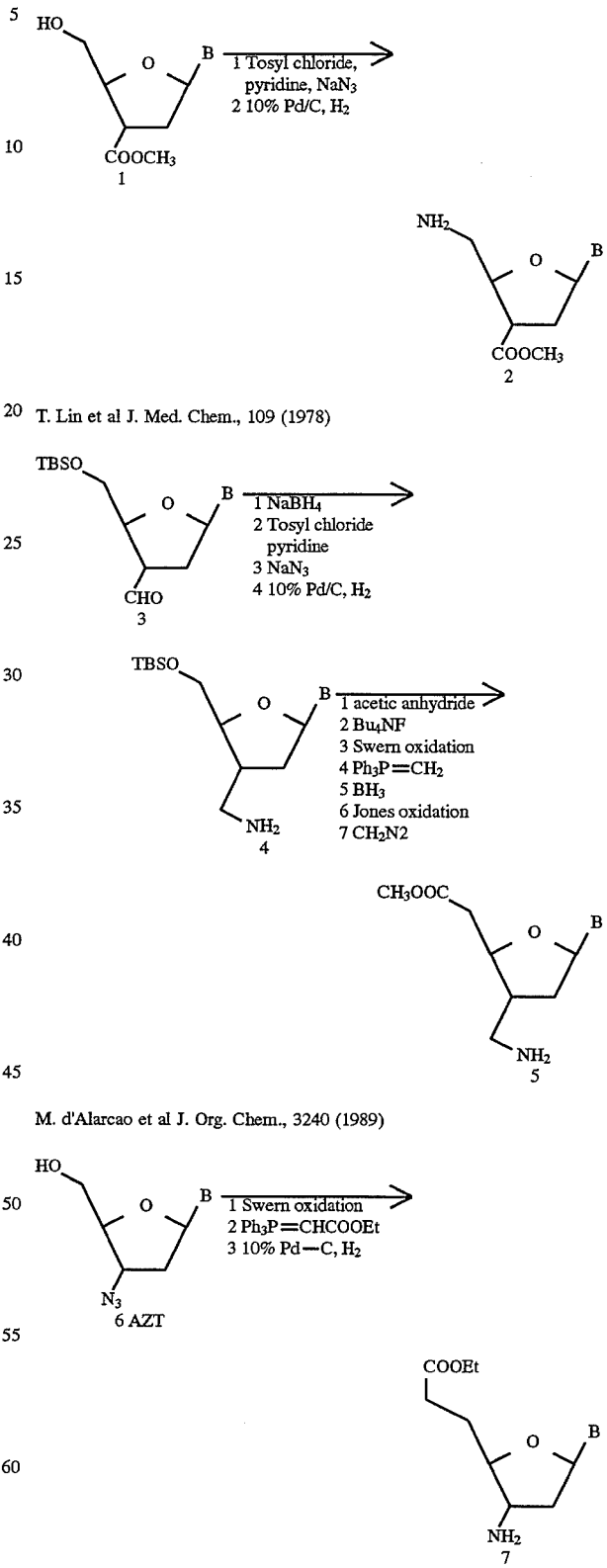

Scheme 1
Bifunctional Intermediates for Amide Linked Trimer, Tetramer, and Longer Oligomers
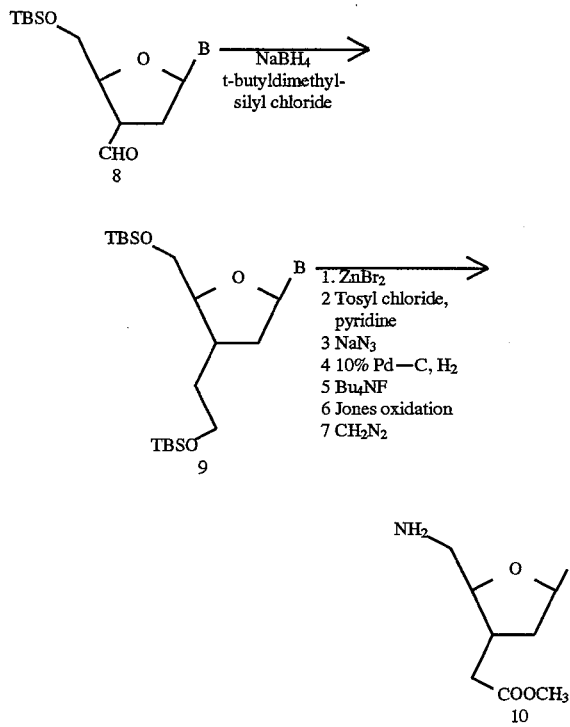
S. Tam, Tet. Lett 597, (1990)
Scheme 2
Synthesis of Amide Linked Dimers, Trimers, and Longer Oligomers
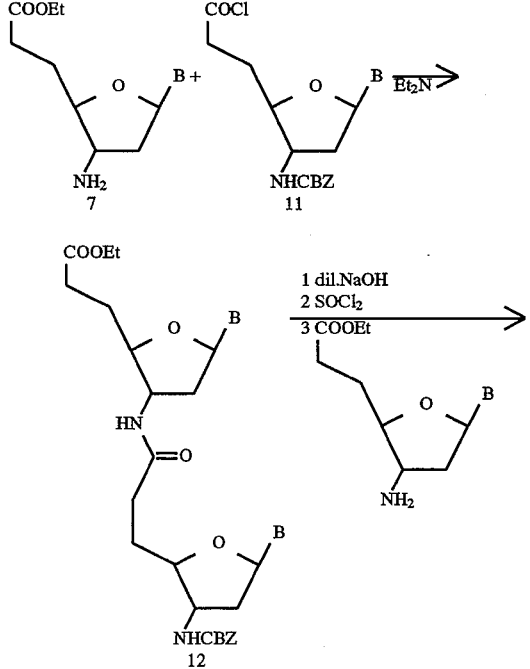
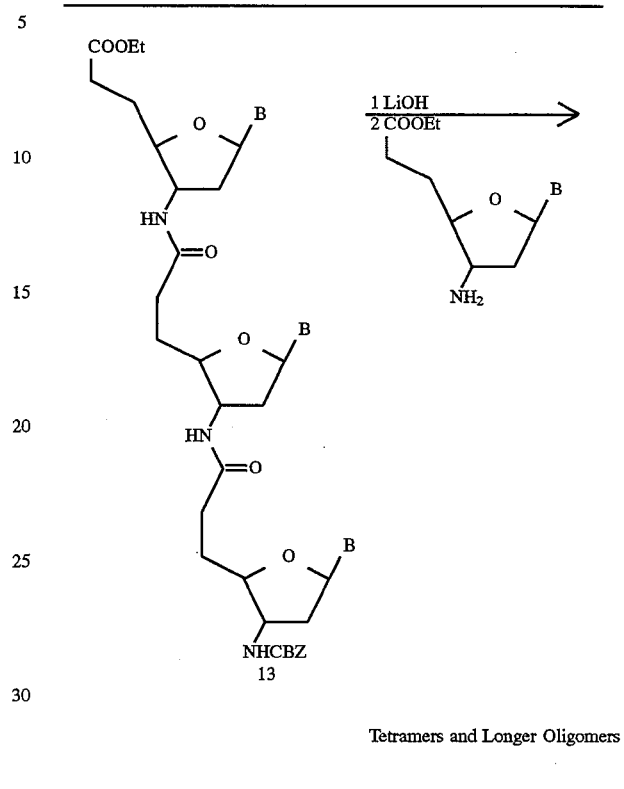
Tetramers and Longer Oligomers -continued
Scheme 2
Synthesis of Amide Linked Dimers, Trimers, and Longer Oligomers

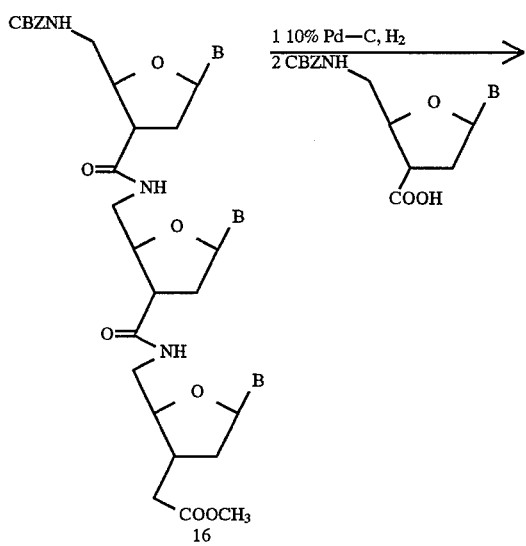

Tetramers and Longer Oligobers

In one embodiment, the compounds of the present invention comprise oligomeric antisense agents of about 3 to about 60 bases, preferably from about 9 to about 50 bases, more preferably from about 12 to about 25 bases, most preferably from 15 to 18 bases. These antisense agents can be formulated into compositions together with one or more non-toxic physiologically acceptable carriers, adjuvants or vehicles which are collectively referred to herein as carriers, for parenteral injection or oral administration, in solid or liquid form, for rectal or topical administration, or the like.

The compositions can be administered to humans and animals either orally, rectally, parenterally (intravenous, intramuscularly or subcutaneously), intracisternally, intravaginally, intraperitoneally, locally (powders, ointments or drops), or as a buccal or nasal spray.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents that delay absorption, for example, aluminum monostearate and gelatin.

Solid dosage forms for oral administration include capsules, tablets, pills, powders and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alginates, gelatin, polyvinylpyrrolidone, sucrose and acacia, (c) humectants, as for example, glylcerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as, for example, quaternary ammonium compounds, (g) wetting agents, as for example, cetyl alcohol and glycerol monostearate, (h) adsorbents, as, for example, kaolin and bentonite, and (i) lubricants, as, for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules, using such excipients as lactose or milk sugar as well as high molecular weight polyethyleneglycols, and the like.

Solid dosage forms such as tablets, dragees, capsules, pills and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, particularly cottonseed oil, ground-nut oil, corn germ oil, olive oil, castor oil and sesame oil, glycerol, tetrahydrofurfuryl alcohol, polyethyleneglycols and fatty acid esters of sorbitan or mixtures of these substances, and the like. Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal or vaginal administration are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and, therefore, melt in the rectum or vaginal cavity and release the active component.

Dosage forms for topical administration include ointments, powders, sprays and inhalants. The active component is admixed under sterile conditions with a physiologically acceptable carrier and any preservatives, buffers or propellants as may be required. Opthalmic formulations, eye ointments, powders and solutions are also contemplated.

Actual dosage levels of the active ingredient in the compositions may be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors.

The total daily dose of the active ingredients administered to a host in single or divided doses may be in amounts, for example, of from about 0.5 mg to about 10 mg per kilogram of body weight. Dosage unit compositions may contain such amounts or such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

The following examples further illustrate the invention and are not to be construed as limiting of the specification and claims in any way.

EXAMPLES

Example 1

5'-Carbethoxymethyl-3'-acetamido-5',3'-dideoxythymidyl-[3'(O)→5'(C)]-3-carbobenzoxyamino-5',3'-dideoxythymidine. (12)

To a solution of 5'-carbethoxymethyl-3'-amino-5',3'-dideoxythymidine (10 mmol) and dicyclohexyl carbodiimide (DCC) (11 mmol) in 50 ml of THF is added dropwise 3'-carbobenzoxyamino-5',3'-dideoxythymidine-5'-acetic acid (11 mmol) in 50 ml of THF with stirring over a 1 hour period. The reaction mixture is filtered and concentrated in vacuo to yield the dimer.

Example 2

5'-Carbethoxymethyl-3'-acetamido-5',3'-dideoxythymidyl[3'(O)→5'(C)]-3'-acetamido-5',3'-dideoxythymidyl[3'(O)→5'(C)]-3-carbobenzoxyamino-5',3'-dideoxythymidine. (13)

The above dimer-ester (12) is saponified with dilute sodium hydroxide and converted to the corresponding dimer-acid chloride with thionyl chloride. Reaction of the latter with 5'-carbethoxymethyl-3'-amino-5',3'-dideoxythymidine affords the title trimer.

Example 3

5'-Carbobenzoxyamino-3'-carbamoyl-5',3'-dideoxythymidyl[3'(O)→5'(C)]-3'-carbomethoxymethyl-5',3'-dideoxythymidine. (15)

To a solution of 5'-amino-3'-carbomethoxymethyl-5',3'-dideoxythymidine 10 (10 mmol) and DCC (11 mmol) in 50 ml of THF is added dropwise 5'-carbobenzoxyamino-5',3'-dideoxythymidine-3'-carboxylic acid (11 mmol) in 50 ml of THF with stirring over a 1 hour period. The reaction mixture is filtered and concentrated in vacuo to yield the dimer.

Example 4

5'-Carbobenzoxyamino-3'-carbamoyl-5',3'-dideoxythymidyl[3'(O)→5'(C)]-3'carbamoyl-5',3'-dideoxythymidyl[3'(O)→5'(C)]-3'-carbomethoxymethyl-5',3'-dideoxythymidine. (16)

The above dimer-ester (15) is hydrogenolyzed with 10% Pd/C to the corresponding dimer-amine. To a solution of the dimer-amine (10 mmol) and DCC (11 mmol) in 50 ml of THF is added dropwise 5'-carbobenzoxyamino-5',3'-dideoxythymidine-3'-carboxylic acid (11 mmol) in 50 ml of THF with stirring over a 1 hour period. The reaction mixture is filtered and concentrated in vacuo to yield the title trimer.

We claim:

1. A compound having the structure of Formula II:

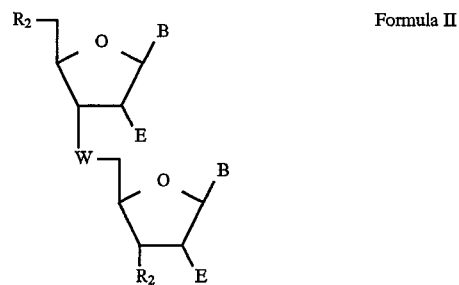

Formula II wherein:

each $R_2$ is selected from the group consisting of H, OH, $NR_3R_4$, CHO, hydroxy-lower alkyl, carbalkoxy-lower alkyl, carboxy- lower alkyl, lower alkenyl, amino-lower alkyl, carbobenzoxyamino, carbobenzoxyamino-lower alkyl, lower alkyl, protected aldehyde and halogen;

each E is selected from the group consisting of H, OZ, SZ, and NHZ;

each Z is selected from the group consisting of H, lower alkyl, lower alkenyl, aryl, acyl, and O-, S-, and N-protecting groups;

each B is independently selected from the group consisting of adenine, cytosine, guanine, thymine, uracil or a modification thereof that does not substantially interfere with the affinity of an oligonucleoside or chimeric oligonucleotide analog for its antisense counterpart wherein the bases are selected from the group consisting of adenine, cytosine, guanine, thymine and uracil;

W is an internucleoside linkage selected from -3'-$(CR_3R_4)_m$-$CONR_1$-$(CR_3R_4)_n$-5'- and -3'-$(CR_3R_4)_m$-$NR_1CO$-$(CR_3R_4)_n$-5'-;

each $R_1$, $R_3$, and $R_4$ is selected from the group consisting of lower alkyl, aryl, aryl-lower alkyl, and lower alkenyl; and m and n are independently 0 or 1, with the proviso that the sum of m+n is 0 or 1.

2. The compound of claim 1 in the form of a salt.

* * * * *